United States Patent [19]
Mehta

[11] Patent Number: 5,476,453
[45] Date of Patent: Dec. 19, 1995

[54] CATHETER FOR SIMULTANEOUS RIGHT AND LEFT CORONARY CANNULIZATION

[76] Inventor: Sameer Mehta, 300 Shore Dr., East, Miami, Fla. 33133

[21] Appl. No.: 246,783

[22] Filed: May 20, 1994

[51] Int. Cl.[6] ................................................. A61M 25/00
[52] U.S. Cl. .......................... 604/281; 128/658; 604/284
[58] Field of Search ...................... 604/95, 264, 284, 604/280–281, 102; 128/656–658

[56] References Cited

U.S. PATENT DOCUMENTS

| | | | |
|---|---|---|---|
| 4,033,331 | 7/1977 | Guss et al. | 604/95 |
| 4,309,994 | 1/1982 | Grunwald | 604/284 |
| 4,748,984 | 6/1988 | Patel | 128/658 |
| 4,769,005 | 9/1988 | Ginsburg et al. | 604/264 |
| 4,790,331 | 12/1988 | Okada et al. | 604/95 |
| 4,909,258 | 3/1990 | Kuntz et al. | 604/102 |
| 4,950,253 | 8/1990 | Jacobs | 604/240 |
| 5,098,412 | 3/1992 | Shiu | 604/280 |
| 5,122,115 | 6/1992 | Marks | 604/280 |
| 5,290,229 | 3/1994 | Paskar | 604/95 |
| 5,299,574 | 4/1994 | Bower | 604/281 |

FOREIGN PATENT DOCUMENTS

| | | | |
|---|---|---|---|
| 0132215 | 1/1985 | European Pat. Off. | 604/264 |

Primary Examiner—John D. Yasko
Assistant Examiner—Mark Bockelman
Attorney, Agent, or Firm—Holland & Knight

[57] ABSTRACT

The Universal Coronary Catheter is a diagnostic coronary catheter which permits simultaneous visualization of the left and right coronary arteries. This is achieved by providing a stationary lumen for cannulating the left coronary artery, and an independently-movable cannula routed through an adjacent lumen for engaging the right coronary artery. The two arms are densely packed within its shaft, the lumen of for cannulating the left coronary artery being about twice the lumen of the cannula. The catheter includes individual lumens for guidewire delivery for injecting radiocontrast agent.

3 Claims, 8 Drawing Sheets

(Prior Art)

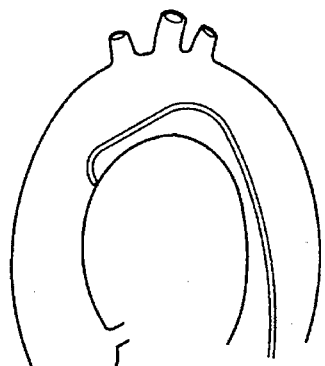
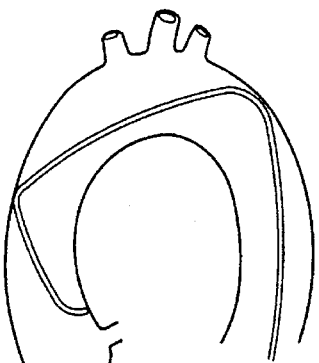
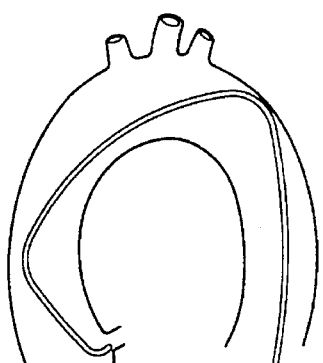
Fig. 3a　　Fig. 3b　　Fig. 3c
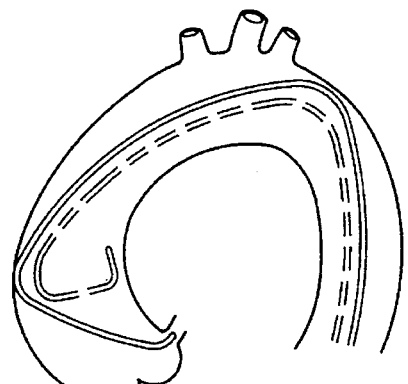
Fig. 3d
(Prior Art)
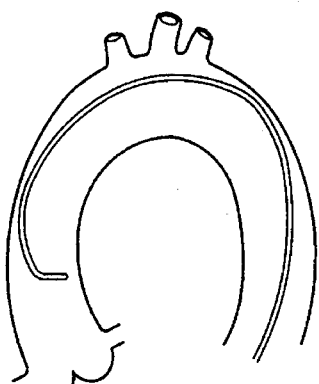
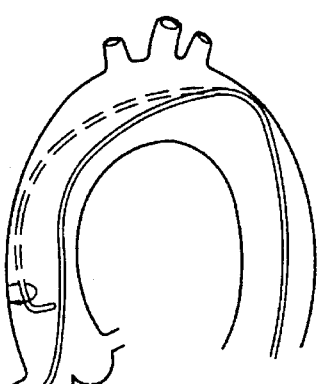
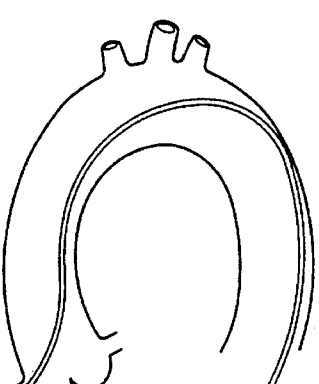
Fig. 4a　　Fig. 4b　　Fig. 4c
(Prior Art)

CATHETER FOR SIMULTANEOUS RIGHT AND LEFT CORONARY CANNULIZATION

FIELD OF THE INVENTION

The invention relates to diagnostic catheters for coronary angiography. More particularly, the present invention relates to a novel coronary angiography catheter capable of simultaneously cannulating the left and right coronary arteries to make possible an angiographic study which clearly demonstrates the entire coronary tree, preferably with a single injection of radiocontrast agent.

BACKGROUND OF THE INVENTION

The diagnosis of coronary artery disease is conclusively made by visualization of coronary arteries in a cardiovascular laboratory. This test, known as coronary angiography, is a part of the more comprehensive procedure of cardiac catheterization. This latter test, besides examining the coronary arteries, also measures pressures in the different heart chambers and assesses the function of the main pumping chamber (left ventricle) of the heart. Cardiac catheterization and coronary angiography were first performed in the United States in 1959. Presently, approximately 800,000 procedures are performed in different cardiovascular laboratories in the country. Results of coronary angiography are crucial for management of coronary artery disease. Based on results of the procedure, the patient is either maintained on medical treatment, referred for bypass surgery or treated with angioplasty. Patients treated with bypass surgery or angioplasty may also require repeat coronary angiography if they again develop symptoms of coronary artery disease.

The procedure of coronary angiography involves first placing a small incision in either the groin or the arm. When performed via the groin, the procedure is called Judkin's technique and this method is much more frequent than the Sones technique which uses either arm. The present invention deals with the Judkin's technique, therefore the following description does not include coronary angiography performed through the arm. After the skin incision is made, the femoral artery is cannulated with the help of a needle. Under x-ray guidance (fluoroscopy) a guidewire is then passed through the needle into the femoral artery. After the guidewire is secured, the needle is withdrawn out of the femoral artery and out of the skin. A thin plastic tube, called the introducer sheath, is next advanced over this guidewire. Continuous access to the arterial system of the body is maintained through the introducer sheath which also provides a arterial channel through which various pre-shaped catheters are advanced. These catheters course from the femoral artery, over and beyond the aortic arch and finally are positioned under fluoroscopic guidance into the coronary arteries. Cannulation of the coronary arteries requires precise manipulation in addition to the simple advancement of the catheters. Operators choose various sequences to cannulate the coronary arteries. In the most common form, a Judkin's Left or JL catheter (FIG. 1) is first employed to cannulate the left coronary artery. Coronary cineangiography of the left coronary artery is then performed by hand injecting iodine-based radiocontrast agent ("dye") into the left coronary artery. The dye opacifies the coronary artery and simultaneous recordings over either videotape or photographic film are made to record results of the x-ray visualization of the contrast opacified coronary arteries. Visualization of coronary arteries in this manner reveals the various blockages (lesions) in the coronary arteries. Several such injections of dye are made in the various radiological projections. Different views are required for clear recognition of the various branches and to overcome confusion which can arise from overlapping of the coronary arteries. After obtaining this information about the left coronary artery, attention is focused on the right coronary artery. To obtain its diagnostic pictures, the JL catheter is exchanged for the Judkin's Right or JR catheter (FIG. 2). The procedure involves disconnecting the JL catheter from the manifold assembly located outside the introducer sheath. The guidewire is next advanced through the JL catheter which is then simultaneously withdrawn out over the guidewire and out of the introducer sheath. With the guidewire now in place, the introducer sheath is flushed with saline and a JR catheter advanced over the guidewire across the aortic arch. The guidewire is then removed and the proximal end of the JR catheter connected to the manifold for recording pressures and for injecting the dye. In comparison to the left coronary artery, the right coronary artery requires more manipulation for engaging its coronary ostium. After the catheter is placed into the origin of the right coronary artery, coronary cineangiography of the right coronary artery is performed in multiple projections in a manner similar to that used to visualize the left coronary artery. Most often a well-performed diagnostic coronary angiography utilizes between six to eight radiographic projections. It also utilizes approximately 100 to 150 milliliters of the radiocontrast agent. FIGS. 3A–3D show a JL catheter cannulating the left coronary artery and FIGS. 4A–4C demonstrate the technique used to cannulate the right coronary artery. FIG. 5 is a drawing of a normal left coronary artery, an illustration of the vessel after injection of dye in the left coronary artery. FIG. 6 similarly shows a normal right coronary artery.

The above mentioned technique is effective in the majority of diagnostic coronary angiography procedures. Although there can be a few technical variations from this standard method, most of the fundamentals are universally applicable. Rarely, a physician may employ a catheter shape other than the JR catheter to cannulate the right coronary artery. This is mostly done in case of unusual coronary anatomy. Another minor technical variation is performed by some operators who chose to completely remove the diagnostic catheter instead of exchanging it over the guidewire. The second catheter is then pre-loaded over the guidewire and advanced to cross the aortic arch when the guidewire is removed and catheterization of the artery performed in the usual fashion. Although standard radiographic projections have been prevalent for several years and are employed by the majority of operators, it is not uncommon to find the use of coronary projections which are somewhat different. Often these are selected by the physician to better highlight the coronary anatomy. On rare occasion, an operator may also decide to first perform angiography of the right coronary artery. Often, evaluation of left ventricular function is also performed in addition to coronary angiography. This is done either before or after cannulation of the coronary arteries with the help of a third type of catheter.

Common denominators besides the above variations which have remained despite decades of coronary angiography procedures include the use of two separate coronary catheters for the left and the right coronary arteries respectively, and the use of multiple radiographic projections to clearly demonstrate the entire coronary anatomy: the three main arteries and their branches.

Although the procedure of cardiac catheterization and coronary cineangiography is relatively safe, complications are present in approximately 1% of cases. Significant both in numbers as well as in their severity are complications resulting from side effects of the radiocontrast agent. All dyes cause renal injury of some degree, they can also induce abnormal heart rhythms (arrhythmias) and precipitate heart failure. There is also a clear linear relationship between the dose of the dye and complications which result from it. Dye-related problems are more commonly encountered in older patients and in patients with diabetes mellitus, kidney failure or with poor function of the left ventricle.

SUMMARY OF THE INVENTION

In sharp contrast to the prevalent techniques of coronary angiography which individually cannulate the left and right coronary arteries, the present invention enables coronary angiography with the aid of a single coronary catheter. It employs a catheter design which simultaneously cannulates the left and right coronary arteries.

A preferred embodiment of a catheter constructed according to the present invention includes an elongated flexible shaft which may be inserted through an incision into an artery, such as the femoral artery, and guided through the artery so as to extend from outside the incision to a position beyond the aortic arch within the heart of a human. The interior of the shaft is divided into a first lumen and a second lumen. The first lumen is preferably larger in cross section than the second lumen and is provided with a connector for coupling the first lumen to a source of fluid such as one including a contrast agent to facilitate imaging. At the distal end of the catheter intended for insertion into the heart, the smaller second lumen terminates in an opening beyond which extends a distal portion of the first lumen. This distal portion of the first lumen is of a size and shape, preferably a Judkins left shape, adopted to facilitate cannulation of the left coronary artery which may then be imaged clearly upon introducing contrast agent by way of the first lumen.

Further in accordance with the invention, the catheter may be provided with a cannula freely slideably and rotatably received within the second lumen and provided at its proximal end with a fluid connector so that the distal end of the cannula can be manipulated independently of the first lumen. The cannula, by manipulation of its proximal end, can be torqued and/or selectively extended from the aforementioned opening of the second lumen and positioned to cannulate the right coronary artery. Once so positioned, the cannula can be used to conduct fluid containing contrast agent to the right coronary artery for imaging while the left artery is simultaneously cannulated by the first lumen.

The coronary angiographic study thus completed clearly demonstrates the entire coronary tree with each coronary injection of radiocontrast agent. Fewer radiological views are required for a complete study and the procedure purposes to reduce the x-ray exposure time and utilize significantly less amounts of dye required for the diagnostic study.

BRIEF DESCRIPTION OF THE DRAWINGS

FIGS. 3A through 3D are partial sectional views of the coronary arch illustrating use of the catheter of FIG. 1 according to the prior art;

FIGS. 4A through 4C are partial sectional views of the coronary arch illustrating use of the catheter of FIG. 2 according to the prior art;

DESCRIPTION OF THE PREFERRED EMBODIMENT

Figure 1:
FIG. 1 is a plan view of a Judkins Left catheter known in the prior art.
Figure 2:
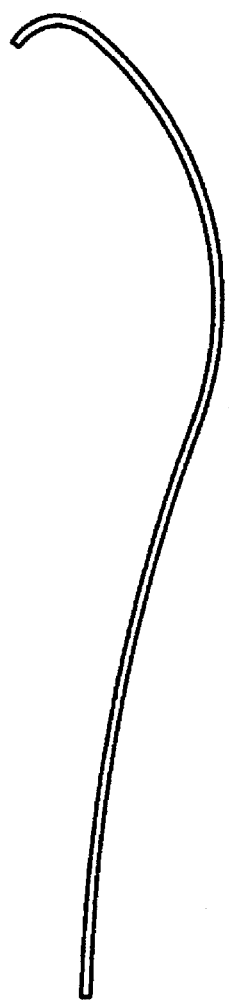
FIG. 2 is a plan view of a Judkins Right catheter known in the prior art.
Figure 5:
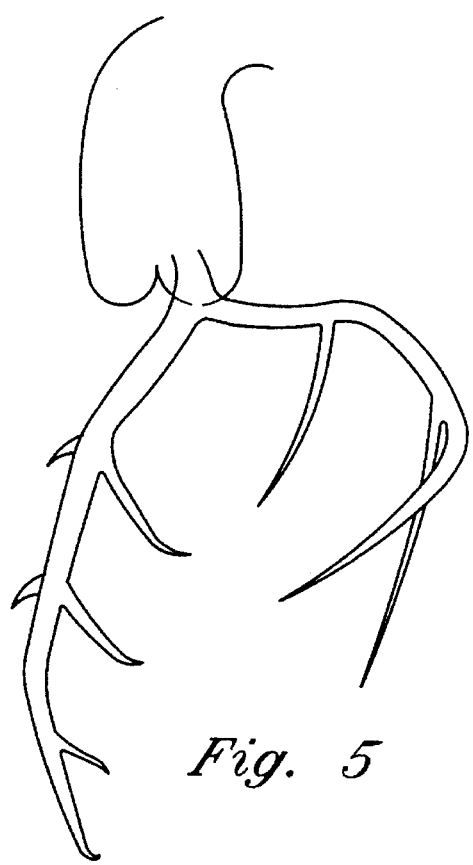
FIG. 5 is a partial sectional view of the coronary arch and the left coronary artery.
Figure 6:
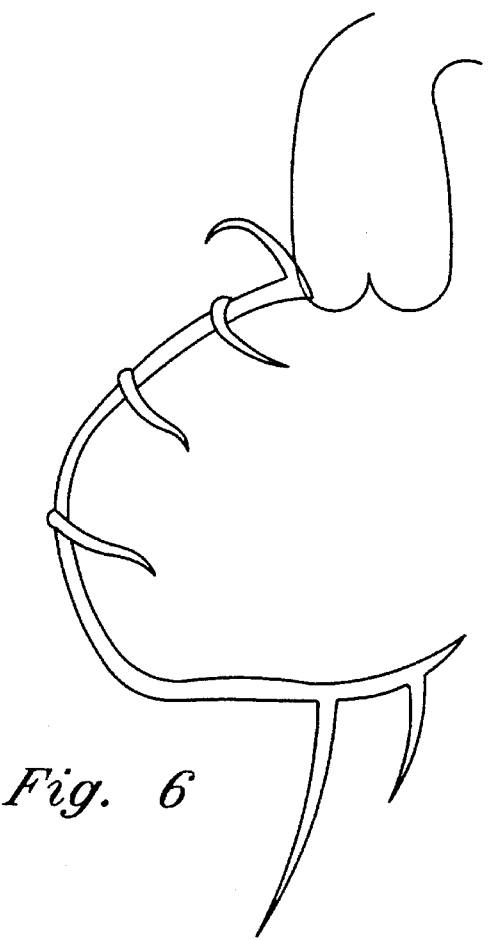
FIG. 6 is a partial sectional view of the coronary arch and the right coronary artery.
Figure 7:
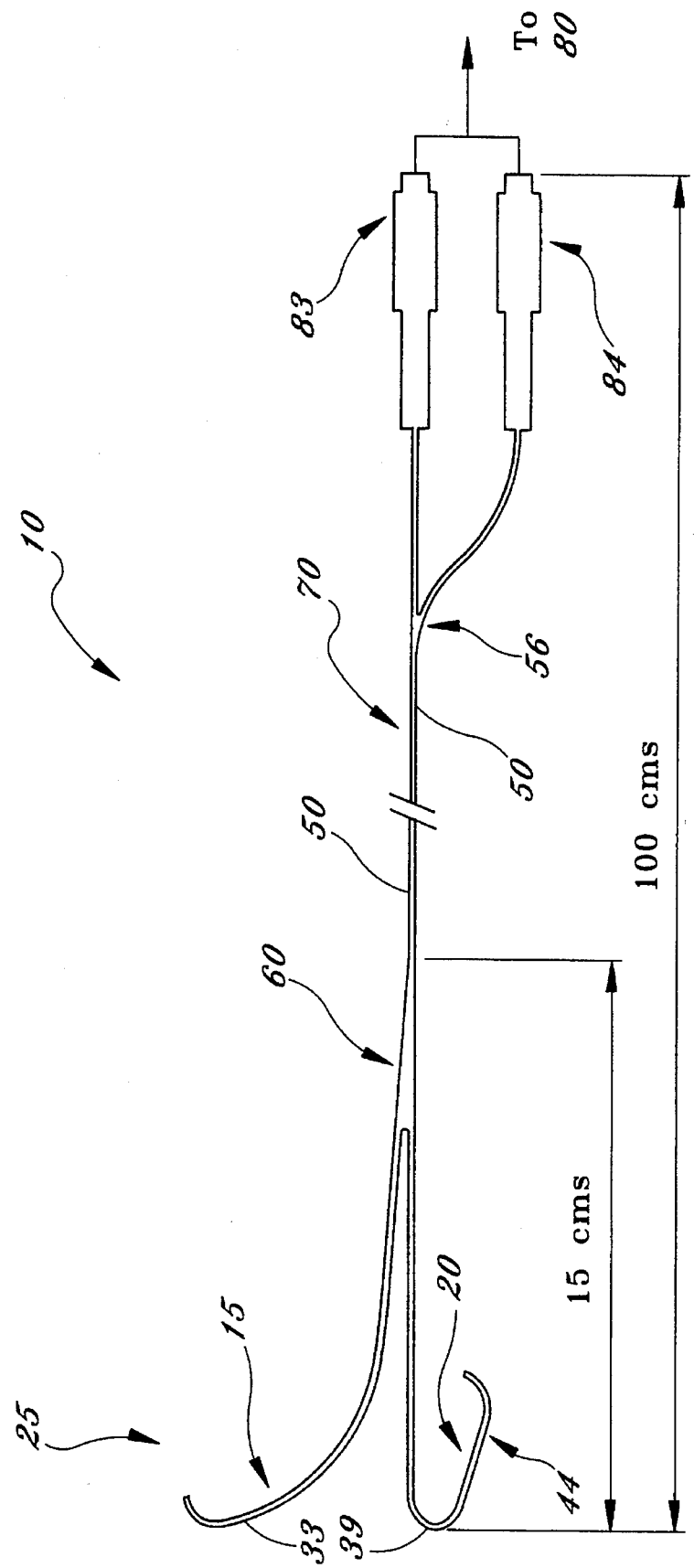
FIG. 7 is a side elevational view of a preferred embodiment of a catheter constructed according to the present invention.
Figure 8:
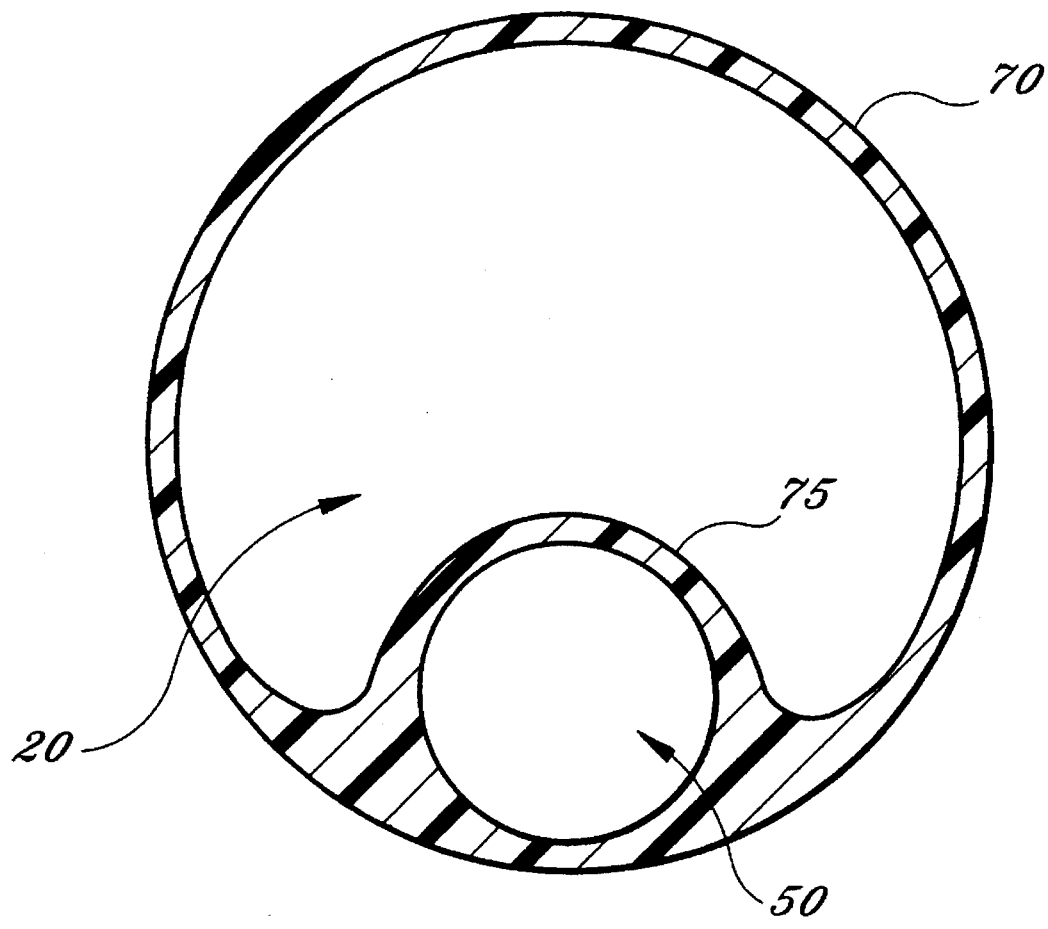
FIG. 8 is a cross sectional view of the shaft of the catheter of FIG. 7 with the cannula withdrawn therefrom.
Figure 9:
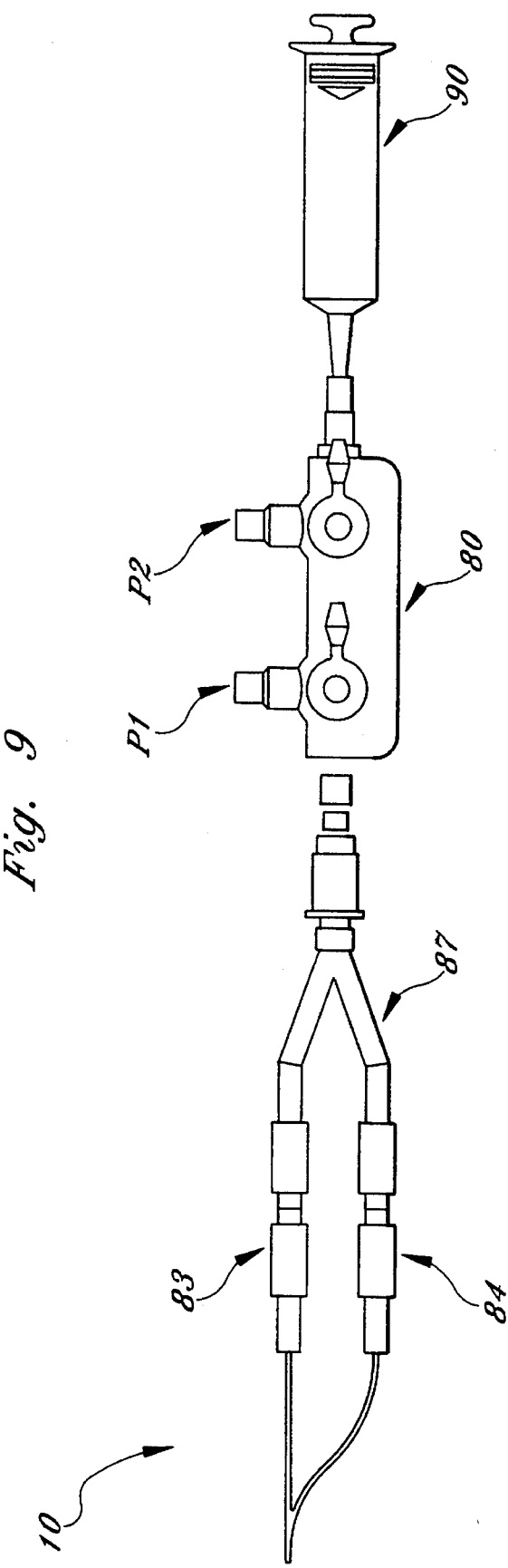
FIG. 9 is a partial side elevational view of the proximal portion of the catheter of FIG. 7 shown coupled to a source of fluid as in a typical use.

FIG. 7 illustrates a preferred embodiment of a catheter 10 constructed according to the present invention. In the form illustrated, catheter 10 is 100 cm long and is constructed from a plastic material which provides tensile strength and torqueability, features which are essential for optimal performance. The design of catheter 10 features two arms, a freely retractable and independently maneuverable cannula 15 and a larger, fixed lumen 20. The distal portion 25 of cannula 15 possesses a right coronary curve 33 for cannulating the right coronary artery. Lumen 20 has a left coronary curve 39 in its distal portion 44 for engaging the left coronary ostium. Movable cannula 15 slides into a second lumen 50 through its proximal portion 56. Lumen 20 and the cannula 15 carried within lumen 50 then remain coaxially oriented until exiting from an opening 60, which in the illustrated embodiment, is located 15 cm from the curve 39 located on the distal portion 44 of lumen 20. Cannula 15 leaves opening 60 and diverges from lumen 20 at this point and remains independently torqueable via its separate proximal portion 65. Lumen 20 is larger in cross section than cannula 15. As FIG. 8 shows, lumen 50 and lumen 20 may be formed within a single shaft 70, the interior of which includes a partition 75. At its proximal portion shaft 70 includes the lumen 50 which receives cannula 15 as well as lumen 20 for radiocontrast agent injections. In the distal portion of shaft 70 beyond opening 60 only the injection lumen 20 remains. Cannula 15 has already diverged from lumen 20 at opening 60. The injection lumen 20 is larger in cross section than the lumen 50 carrying cannula 15 and is therefore necessarily larger than the flow cross section of cannula 15 itself. This provides greater flow through lumen 20 than through cannula 15. Such flow differential is desirable in view of the fact that the left coronary artery is generally larger than the right coronary artery. The cross sectional design (FIG. 8) of the tube 70 of catheter 10 reveals dense packing of lumina 20 and 50. Lumen 20 is shaped in the form of a kidney-bean and lumen 50 is of a circular shape which fits snugly in the concave portion of the kidney-bean configuration of lumen 20. Orientation in this manner enables construction of catheter 10 in small French sizes (5 and 6 F). At their proximal portions, 83 and 65 respectively, lumen 20 and cannula 15 are joined to a manifold 80 via a Y connector 87 (FIG. 9). This manifold 80 has two ports, P1 for monitoring arterial pressure and P2 for dye delivery. The distal end of the manifold is connected to a 20 ml. plastic syringe 90.

Figure 10:
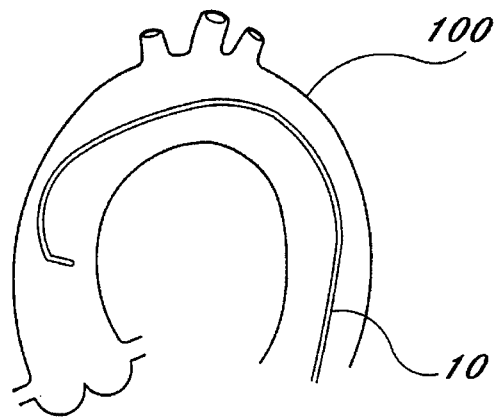
FIG. 10 is a partial sectional view of the coronary arch illustrating introduction of the distal portion of the catheter of FIG. 7.
Figure 11:
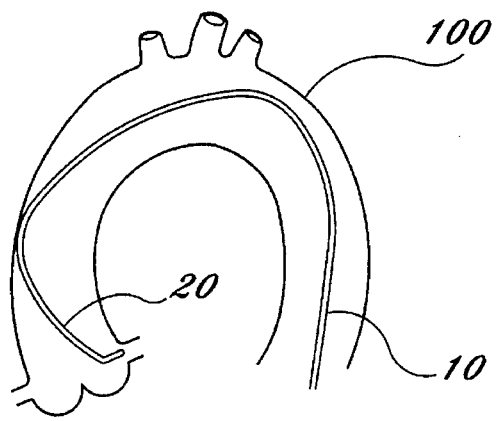
FIG. 11 is a partial sectional view of the coronary arch illustrating cannulation of the left branch of the coronary artery by the distal portion of the first lumen of the catheter of FIG. 7.
Figure 12:
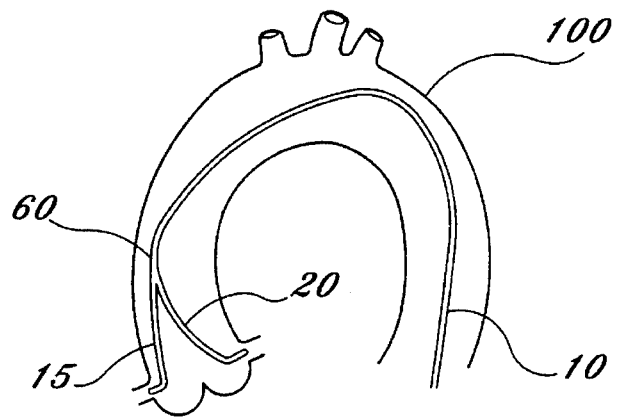
FIG. 12 is a partial sectional view of the coronary arch showing the distal end of the cannula of the catheter of FIG. 7 extended and positioned to cannulate the right branch of the coronary artery while the left branch is at the same time cannulated by the first lumen thereof.

FIGS. 10–12 demonstrate the simple technique which is used to obtain coronary angiography using the catheter 10. The femoral artery is cannulated in the customary fashion described previously and an arterial introducer sheath is placed. A guidewire (not shown) is advanced through this sheath and advanced over the aortic arch 100. Catheter 10 is advanced, with its cannula 15 retracted, over this guidewire and positioned across the aortic arch 100. The guidewire is next removed and the proximal portion of the catheter 10 connected to the manifold 80 as described above. This manifold 80 permits maintenance of a closed system during pressure monitoring, flushing of catheter 10 and contrast agent administration. The catheter 10 is immediately double flushed: blood is withdrawn and discarded, and heparinized saline flush is injected through the catheter 10. Once the catheter 10 has been flushed with saline solution, tip pressure is monitored at all times except during contrast injections. Catheter 10 is then advanced around the aortic arch 100 into the ascending aorta under continuous pressure monitoring and fluoroscopic imaging. During this maneuver as well as during cannulating the left coronary artery, the distal curved portion 33 of cannula 15 remains withdrawn into the lumen 50. Cannulation of the left coronary artery is first performed: lumen 20 is continuously maintained en face as it is advanced into the aortic root. In the majority of cases, the lumen 20 of catheter 10 engages the left coronary ostium without requiring any additional manipulations. Engagement is constantly attempted with lumen 20 traversing the ascending aorta at an angle of approximately 45 degrees, the tip of the catheter 10 in almost a horizontal plane, and with no change in the pressure waveform or the readout numbers recorded from the catheter tip. After stable cannulation of the left coronary artery is achieved with lumen 20 of catheter 10 engagement of the right coronary artery is performed. The left anterior oblique view is chosen for this purpose.

Figure 13:
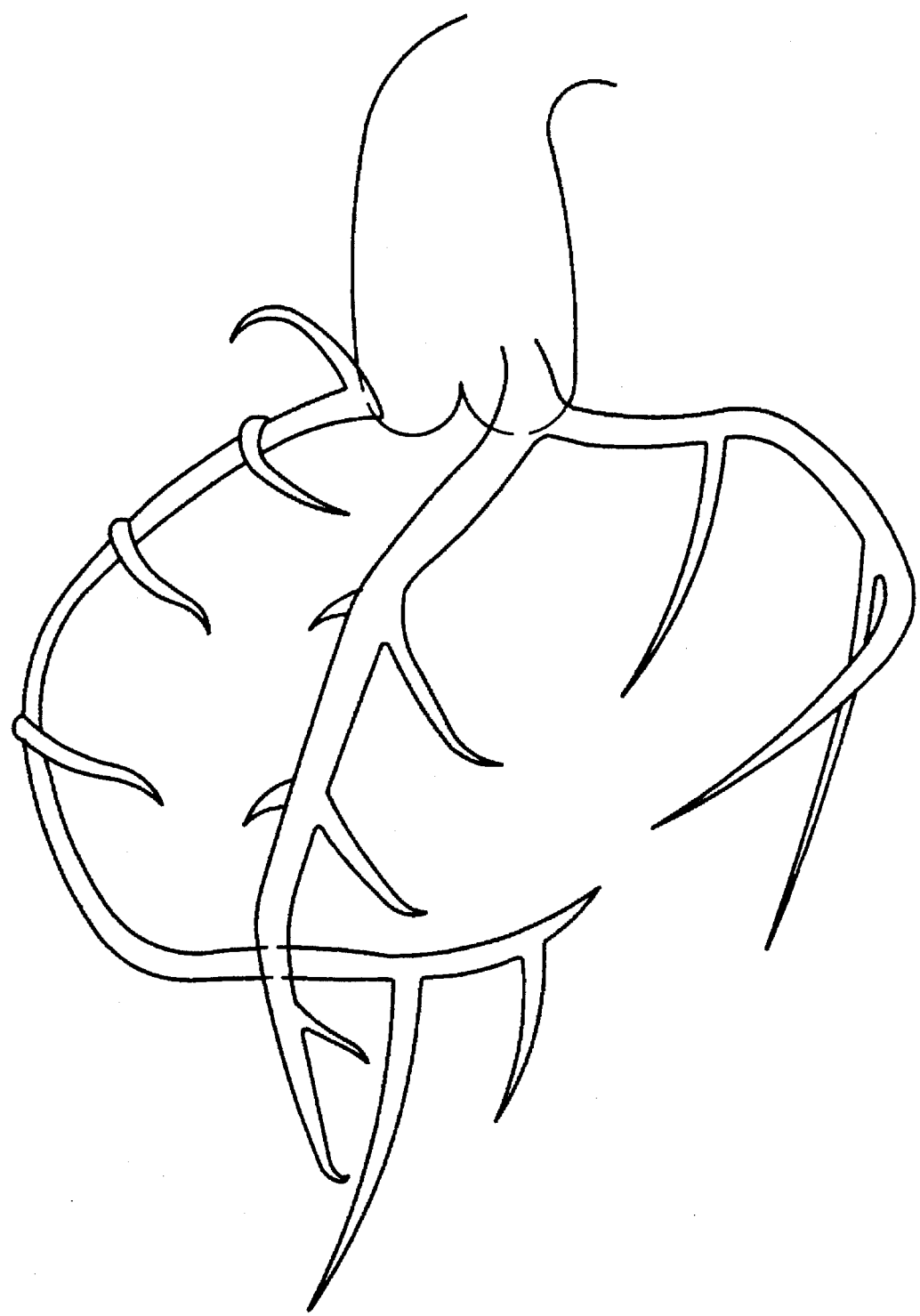
FIG. 13 is a partial sectional view of the coronary arch and the right and left branches of the coronary artery.

The cannula 15 of catheter 10, which is designed to maintain independent maneuverability, is now advanced forward from opening 60 at the exit point of lumen 50. By torquing from its independent proximal hub, cannula 15 is brought around the aortic arch 100 with its tip facing inwards and lying against the right side of the aortic arch aimed at the left coronary ostium. The cannula 15 is then rotated clockwise by nearly 180 degrees to engage the right coronary artery. As with the left arm, this is achieved without any diminishing of the arterial pressure. After stable cannulation of the left and right coronary arteries is achieved with the L and the R arms respectively, coronary injections are made via the manifold by hand-held syringe injections. FIG. 13 shows a sample diagram of the left and right coronary arteries after the simultaneous injection of radiocontrast agent into both coronary arteries. For a routine case, only two coronary projections may be required; a RAO (right anterior oblique) 30 degrees view and a LAO (left anterior oblique) 60 degree projection. In the majority of cases these two views will adequately demonstrate the entire coronary arterial tree and highlight the coronary lesions.

If significant manipulations are required to cannulate either the left or the right coronary artery, a guidewire (not shown) can be individually passed through their separate lumens. Intubation of the coronary arteries is thus simplified and severe catheter torquing eliminated. Certain anatomical variations will require different sizes of the catheter 10 of the invention. The size mentioned in the above description is the commonest variety: a size 4, the number 4 representing the 4 cm curve on the distal portions of both the lumen 20 and cannula 15 of catheter 10. For patients with enlarged aortic roots, a size 5 catheter 10 is recommended. In this situation, as seen with the size 4, the number 5 denotes the size in cm. of the curves 33 and 39 on the lumen 20 and cannula 15 respectively. Similarly, for small aortic roots, the size 3 catheter 10 is recommended: the distal tips of the lumen 20 and cannula 15 in this catheter 10 are 3 cm each. Besides the varying size of the aortic root that requires non-4 size catheters, marked tortuosity, large coronary arteries of different anatomical positions (different axis or size) of the heart may require utilization of additional radiological projections for the precise definition of coronary lesions. As with the use of JL and JR catheters, such views are determined by individual operators.

Although the cather 10 of the invention has been designed for performing diagnostic coronary angiography, certain other advantages ensue from its unique design characteristics. Without considerable alteration of the basic design or procedure, it is also possible to completely withdraw the cannula 15 of the catheter 10 and replace it by a specially shaped catheter (called the pigtail catheter) through which left ventriculography can be performed. To use the catheter 10 for this purpose, catheter 10 is first placed over the aortic arch 100. The pigtail catheter (not shown) is then advanced into the left ventricle while the lumen 20 is kept stationary. Left ventriculography is then performed and after obtaining pull-back pressure measurements across the aortic valve, the pigtail catheter is removed from the cather 10 and replaced by cannula 15. Coronary angiography is then performed with the technique which has been described above.

It is conceived that the catheter 10 of the invention will provide excellent demonstration of the coronary artery anatomy in virtually every patient for whom it is employed. However, in situations with severe left main coronary artery disease or with ostial right coronary artery disease, severe arterial pressure dampening may result. In these conditions, switching to the customary Judkin's technique is recommended for individual cannulation of the left and right coronary arteries.

In view of the foregoing, it can be appreciated that the invention provides for diagnosis of coronary artery disease using a single catheter 10 insertable through a single incision. Moreover, use of the invention allows such diagnosis to be performed while exposing the patient to lesser amounts of radiocontrast agent and lower doses of imaging radiation than would otherwise be required. By permitting simultaneous imaging of the left and right coronary arteries, the invention provides more comprehensive information concerning the condition of the coronary arteries of the patient with each injection of radiocontrast agent and provides for differential flow rates of radiocontrast agent in the left and right coronary arteries as well as with different quantities of dyes simultaneously injected into the left and right coronary arteries. As noted above, the invention is also readily adaptable to perform left ventriculography.

While the foregoing constitutes a preferred embodiment of the invention, according to the best mode presently contamplated by the inventor of making and carrying out the invention, it is to be understood that the invention is not limited to the embodiment which has been described. In light of the present disclosure, various alternative embodiments will be apparent to those skilled in the art. Accordingly, it is to be recognized that changes can be made without departing from the scope of the invention as particularly pointed out and distinctly claimed in the appended claims as interpreted literally or expanded to include all legal equivalents.

What is claimed is:

1. A coronary catheter for simultaneously cannulating both a right coronary artery and a left coronary artery, said catheter comprising:

an elongated, flexible shaft having a hollow interior which is divided along at least a portion of the length of said shaft into a first lumen and a second lumen, each of said lumina having a proximal end, said proximal end of said first lumen being coupleable to a source of fluid, said second lumen terminating in an opening spaced from said proximal end of said second lumen, said first lumen having a distal shaft portion extending beyond said opening, said distal shaft portion having a preformed left coronary curve shape for traversing the aortic arch from the descending aorta and cannulating the left coronary artery of a human by said first lumen whereby fluid from the source may be introduced into the left coronary artery by way of said first lumen, and a cannula having a distal end having a preformed right coronary shape for traversing the aortic arch from the descending aorta and cannulating the right coronary artery and a proximal end, said proximal end being coupleable to the source of fluid, at least a portion of the length of said cannula being freely rotatably and freely slidably received within said second lumen whereby through manipulation of said proximal end of said cannula, said distal end of said cannula may be selectively extended from said opening of said second lumen and positioned to traverse the aortic arch and to cannulate the right coronary artery so as to permit introduction of fluid from the source into the right coronary artery while the left coronary artery is cannulated by said distal end of said first lumen.

2. The catheter of claim 1 wherein said second lumen has a cross sectional area greater than that of said cannula.

3. The catheter of claim 1 wherein said first lumen and said second lumen are formed within a common shaft generally circular in cross section and said first lumen is of a generally kidney-shaped cross section including a convex portion within which at least a portion of the cross-section of said second lumen is nested.

* * * * *